United States Patent
Nakacho et al.

(10) Patent No.: US 6,528,559 B1
(45) Date of Patent: Mar. 4, 2003

(54) CROSSLINKED PHENOXYPHOSPHAZENE COMPOUNDS, PROCESS FOR THE PREPARATION THEREOF, FLAME RETARDANTS, FLAME-RETARDANT RESIN COMPOSITIONS, AND MOLDINGS OF FLAME-RETARDANT RESINS

(75) Inventors: Yoshifumi Nakacho, Tokushima (JP); Tadao Yabuhara, Tokushima (JP); Yuji Tada, Tokushima (JP); Yoichi Nishioka, Tokushima (JP)

(73) Assignee: Otsuka Chemical Co., Ltd., Osaka (JP)

( * ) Notice: Subject to any disclaimer, the term of this patent is extended or adjusted under 35 U.S.C. 154(b) by 0 days.

(21) Appl. No.: 09/762,637

(22) PCT Filed: Aug. 5, 1999

(86) PCT No.: PCT/JP99/04256

§ 371 (c)(1),
(2), (4) Date: Feb. 12, 2001

(87) PCT Pub. No.: WO00/09518

PCT Pub. Date: Feb. 24, 2000

(30) Foreign Application Priority Data

Aug. 13, 1998 (JP) ............................................. 10-228897
Sep. 2, 1998 (JP) ............................................. 10-248415

(51) Int. Cl.$^7$ ............................. C08K 5/15; C08K 21/00
(52) U.S. Cl. ........................ 524/116; 524/708; 252/609; 558/80; 558/92; 558/93; 558/200
(58) Field of Search ........................... 252/609; 524/95, 524/98, 99, 116, 708; 558/80, 92, 93, 200

(56) References Cited

U.S. PATENT DOCUMENTS

| | | |
|---|---|---|
| 4,094,856 A | 6/1978 | Guschl |
| 4,117,041 A | 9/1978 | Guschl |

FOREIGN PATENT DOCUMENTS

| | | |
|---|---|---|
| GB | 1425853 | 2/1976 |
| GB | 1436352 | 5/1976 |
| GB | 1468799 | 3/1977 |
| GB | 1512966 | 6/1978 |
| JP | 50-34097 | 4/1975 |
| JP | 52-119700 | 10/1977 |
| JP | 52-153987 | 12/1977 |
| JP | 53-98359 | 8/1978 |
| JP | 11-255876 | 9/1999 |
| WO | WO 99 19383 | 4/1999 |

*Primary Examiner*—Kriellion A. Sanders
(74) *Attorney, Agent, or Firm*—Sughrue Mion, PLLC

(57) ABSTRACT

This invention provides a halogen-free flame retardant which advantageously has a high melting point and a low volatility and does not impair the inherent properties of resins. The flame retardant of the invention is a phosphazene compound crosslinked with a crosslinking group such as a phenylene group, wherein each of the crosslinking groups is interposed between the two oxygen groups left after the elimination of phenyl groups from the phosphazene compound; the crosslinked phenoxyphosphazene compound does not have any free hydroxyl groups (derived from crosslinking groups); and the amount of the phenyl groups in the crosslinked compound is 50 to 99.9%, based on the total number of the phenyl groups in the phosphazene compound.

14 Claims, No Drawings

CROSSLINKED PHENOXYPHOSPHAZENE COMPOUNDS, PROCESS FOR THE PREPARATION THEREOF, FLAME RETARDANTS, FLAME-RETARDANT RESIN COMPOSITIONS, AND MOLDINGS OF FLAME-RETARDANT RESINS

FIELD OF THE INVENTION

The present invention relates to crosslinked phenoxyphosphazene compounds, a process for the preparation thereof, flame retardants, flame-retardant resin compositions and moldings of flame-retardant resins.

BACKGROUND ART

Synthetic resins are widely used in various fields such as electric and electronic products, office automation equipment, office equipment and communications equipment because of their excellent molding processability, mechanical properties, appearance and the like. The resins used in certain applications are required to have flame retardancy for protection against the heat and ignition of internal parts in devices and appliances.

In order to impart flame retardancy to synthetic resins, a flame retardant is generally added to the resin prior to molding of the resin. Flame retardants are roughly classified into two groups, i.e., halogen-containing flame retardants and halogen-free flame retardants.

Examples of halogen-containing flame retardants include tetrabromobisphenol-A and like organic halogen compounds; tris(chloroethylphosphate), tris(2,3-dibromopropyl) phosphate and like halogen-containing organic phosphorus compounds. Halogen-containing flame retardants produce high flame-retardant effects but also reduce heat stability of matrix synthetic resins, cause deterioration and discoloration of the resins and further have the following drawbacks. Halogen-containing flame retardants undergo thermal decomposition to generate hydrogen halide, thereby causing corrosion of metallic molds, and further produce low molecular weight toxic halogen compounds as byproducts during molding or burning.

Examples of halogen-free flame retardants include magnesium hydroxide, aluminum hydroxide and like inorganic metal hydroxides; triphenyl phosphate (TPP), resorcinol bis(diphenylphosphate)(RDPP), trixylyl phosphate (TXP) and like organic phosphorus compounds (EP Patent No. 174,493, Dutch Patent No. 8,802,346, Japanese Unexamined Patent Publication No. 1,079/1993 and U.S. Pat. No. 5,122,556).

The inorganic metal hydroxides exhibit flame retardancy due to water generated by thermal decomposition. Since water merely produces low flame retardant effects, the inorganic metal hydroxide must be added in a large amount to provide a sufficient level of flame retardancy. However, such a large amount addition entails a disadvantage that the inherent properties of synthetic resins (e.g., mechanical properties) are impaired.

The organic phosphorus compounds produce comparatively high flame-retardant effects. However, since these compounds are liquid or low melting solid and have a high volatility, it is necessary to use a low temperature for molding a resin composition containing an organic phosphorus compound, and there always arise problems such as blocking during kneading, and migration of the organic phosphorus compound to the surface (juicing) during kneading or molding. Moreover, resin compositions containing said organic phosphorus compound have the drawback of dripping (falling of molten resin droplets) during burning and spreading of a fire due to the dripping. Consequently, in order to obtain a rating of V-0 (flaming does not continue for more than a specified period, and there are no molten resin drips which ignite cotton) in a flame retardancy test UL-94 (Testing for Flammability of Plastic Materials for Parts in Devices & Appliances, which is a standard test for evaluating flame retardancy), by adding an organic phosphorus compound to a resin, it is necessary to add a fluorine-containing resin such as polytetrafluoroethylene (PTFE) as an agent for preventing dripping of molten resin during burning. However, the fluorine-containing resin contains halogen and evolves toxic gases during combustion.

Known as flame retardants are phenoxyphosphazene compounds obtained by reacting dichlorophosphazene with a monohydroxy compound such as phenol. For example, proposed is adding a phenoxyphosphazene compound to a thermoplastic resin, such as polyamide resin (Japanese Examined Patent Publication No. 53,746/1981), polycarbonate resin (Japanese Unexamined Patent Publication No. 37,149/1976), polycarbonate or a mixture of polycarbonate and other thermoplasitic resins (Japanese Unexamined Patent Publication No. 292,233/1995) or a mixture of aromatic polycarbonate and rubber-styrene resin (Japanese Unexamined Patent Publication No. 53,009/1997), or to a thermosetting resin such as epoxy resin (Japanese Unexamined Patent Publication No. 225,714/1996).

Such incorporation of phenoxyphosphazene may increase the limit oxygen index (LOI) value (an index of flame retardancy) but does not impart sufficiently improved flame retardancy to the resin and inevitably reduces heat resistance and mechanical properties of the resin.

Further, Japanese Unexamined Patent Publication No. 47,042/1976 proposes using as a thermoplastic aromatic polyester flame retardant a phosphazene compound prepared by substituting chlorine atoms of dichlorophosphazene with monohydroxy compounds (e.g., alkali metal phenolate) so as to have a substitution degree of 3.9 to 6 (based on the dichlorophosphazene trimer) and further substituting the residual chlorine atoms with alkali metal diphenolate (e.g., an alkali metal salt of 4,4'-isopropylidene diphenol).

However, when the phosphazene compound prepared by the production method disclosed therein is incorporated into a thermoplastic resin such as polyester or polycarbonate, the molecular weight of the thermoplastic resin decreases and moldings of the resulting resin composition will have low mechanical properties and low heat resistance and fail to have a sufficiently high flame retardancy. This tendency becomes more evident with the lapse of time from the production of the resin moldings.

DISCLOSURE OF THE INVENTION

An object of the present invention is to provide a novel phosphazene compound which can greatly improve flame retardancy.

Another object of the invention is to provide a flame retardant which, when incorporated into a thermoplastic resin or a thermosetting resin, does not reduce the molecular weight of the resin and thus does not impair the mechanical properties or heat resistance of the resin.

A further object of the invention is to provide a process for preparing the foregoing phosphazene compound.

Other features of the present invention will become apparent from the following description.

The present inventors carried out extensive research to achieve the above objects, and finally succeeded in producing a new crosslinked phenoxyphosphazene compound which is useful as a flame retardant for synthetic resins, and completed the present invention.

According to the present invention, there is provided a crosslinked phenoxyphosphazene compound characterized in that:

at least one phosphazene compound selected from the group consisting of a cyclic phosphazene compound represented by the formula (1)

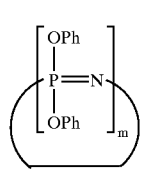

(1)

(wherein m is an integer of 3 to 25 and Ph is a phenyl group) and a straight- or branched-chain phosphazene compound represented by the formula (2)

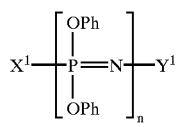

(2)

(wherein $X^1$ represents a group —N=P(OPh)$_3$ or a group —N=P(O)OPh, $Y^1$ represents a group —P(OPh)$_4$ or a group —P(O)(OPh)$_2$, and n is an integer of 3 to 10000 and Ph is as defined above)

is crosslinked with at least one crosslinking group selected from the group consisting of o-phenylene group, m-phenylene group, p-phenylene group and bisphenylene group represented by the formula (3)

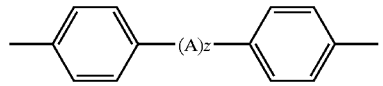

(3)

(wherein A is —C(CH$_3$)$_2$—, —SO$_2$—, —S— or —O— and z is 0 or 1);
  (a) each of the crosslinking groups is interposed between the two oxygen atoms left after the elimination of phenyl groups from the phosphazene compound;
  (b) the amount of the phenyl groups in the crosslinked compound is 50 to 99.9% based on the total amount of the phenyl groups in said phosphazene compound represented by the formula (1) and/or said phosphazene compound represented by the formula (2); and
  (c) the crosslinked phenoxyphosphazene compound has no free hydroxyl groups in the molecule.

According to the present invention, there is provided a process for preparing the foregoing crosslinked phenoxyphosphazene compound which comprises the following steps:

at least one dichlorophosphazene compound selected from the group consisting of a cyclic dichlorophosphazene compound represented by the formula (4)

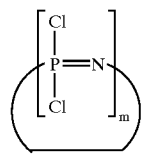

(4)

(wherein m is as defined above) and a straight- or branched-chain dichlorophosphazene compound represented by the formula (5)

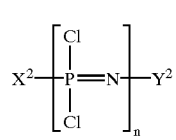

(5)

(wherein $X^2$ represents a group —N=PCl$_3$ or a group —N=P(O)Cl, $Y^2$ represents a group —PCl$_4$ or a group —P(O)Cl$_2$, and n is as defined above) is reacted with a mixture of alkali metal phenolate represented by the formula (6)

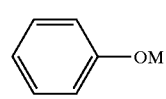

(6)

(wherein M is an alkali metal) and at least one diphenolate selected from the group consisting of alkali metal diphenolate represented by the formula (7)

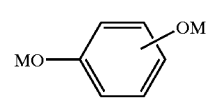

(7)

(wherein M is as defined above) and alkali metal diphenolate represented by the formula (8)

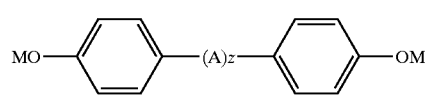

(8)

(wherein A, z and M are as defined above); and
the resulting compound is further reacted with the alkali metal phenolate.

The crosslinked phenoxyphosphazene compound of the invention produces higher flame retardant effects than conventional non-crosslinked phenoxyphosphazene compounds and imparts high flame retardancy to thermoplastic resins or thermosetting resins.

The crosslinked phenoxyphosphazene compound of the invention which is free of halogen does not cause corrosion of metallic molds or deterioration or discoloration of resins during molding and does not produce any toxic gases such as hydrogen halide during combustion.

Furthermore, the crosslinked phenoxyphosphazene compound of the invention which has a low volatility does not necessitate using a low resin molding temperature and is free of shortcomings such as blocking during kneading, migration of the flame retardant to the surface (juicing) during kneading or molding, and dripping during burning.

The present inventors carried out research and found that the phosphazene compound prepared by the method disclosed in the foregoing Japanese Unexamined Patent Publication No. 47,042/1976 has residual free hydroxyl groups derived from the starting material alkali metal diphenolate in the molecule. The present inventors further found that when a phosphazene compound containing such free hydroxyl groups is incorporated into a thermoplastic resin such as polyester or polycarbonate, the free hydroxyl groups cause the reduction of the molecular weight of the resin, and moldings of the resulting resin composition will have inferior mechanical properties and heat resistance.

The crosslinked phenoxyphosphazene compound of the invention having no free hydroxyl groups in the molecule does not reduce the molecular weight of synthetic resins and thus does not impair molding processability of synthetic resins or mechanical properties (e.g., impact resistance) and heat resistance of synthetic resin moldings.

In this specification, "having no free hydroxyl groups in the molecule" means that the amount of free hydroxyl groups is less than the detectable limit, when measured according to the acetylation method using acetic anhydride and pyridine as described on page 353 of Analytical Chemistry Handbook (revised 3rd edition, edited by Japan Analytical Chemistry Academy, published by Maruzen Book Store Co., Ltd., 1981). Herein the term "detectable limit" means the minimum amount detectable as hydroxyl equivalents per gram of a test sample (crosslinked phenoxyphosphazene compound of the invention), more specifically $1 \times 10^{-6}$ hydroxyl equivalents/gram.

On analysis of the crosslinked phenoxyphosphazene compound of the invention by the foregoing acetylation method, the resulting amount includes the amount of hydroxyl groups in the residual phenol used as a starting material. Since the quantity of the starting material phenol can be determined by high speed liquid chromatography, the amount of free hydroxyl groups in the crosslinked phenoxyphosphazene compound can be precisely determined.

The present invention provides a flame retardant comprising the aforementioned crosslinked phenoxyphosphazene compound as an active ingredient.

The present invention further provides a flame-retardant resin composition comprising 100 wt. parts of a thermoplastic resin or a thermosetting resin and 0.1 to 100 wt. parts of the aforementioned flame retardant.

The present invention further provides a flame-retardant resin composition comprising 100 wt. parts of a thermoplastic resin or a thermosetting resin, 0.1 to 100 wt. parts of the aforementioned flame retardant and 0.01 to 50 wt. parts of an inorganic filler.

The present invention also provides a flame-retardant resin composition comprising 100 wt. parts of a thermoplastic resin or a thermosetting resin, 0.1 to 50 wt. parts of the aforementioned flame retardant, and 0.1 to 50 wt. parts of an organic phosphorus compound free of halogen.

The present invention further provides a flame-retardant resin composition comprising 100 wt. parts of a thermoplastic resin, 0.1 to 100 wt. parts of the aforementioned flame retardant and 0.01 to 2.5 wt. parts of a fluorine-containing resin.

Further, the present invention provides flame-retardant resin molded articles produced by molding any of the above flame-retardant resin compositions.

Crosslinked Phenoxyphosphazene Compounds

The crosslinked phenoxyphosphazene compounds of the invention can be obtained by a process comprising the following two steps:

at least one dichlorophosphazene compound selected from the group consisting of a cyclic dichlorophosphazene compound represented by the formula (4) and a straight- or branched-chain dichlorophosphazene compound represented by the formula (5) is reacted with a mixture of alkali metal phenolate represented by the formula (6) and at least one diphenolate selected from the group consisting of alkali metal diphenolate represented by the formula (7) and alkali metal diphenolate represented by the formula (8) (the first step); and the resulting compound is further reacted with the alkali metal phenolate (the second step).

The study of the present inventors revealed that alkali metal diphenolate represented by the formula (7) or (8) reacts with dichlorophosphazene compounds much less than alkali metal phenolate represented by the formula (6). More specifically, when a mixture of a dichlorophosphazene compound and alkali metal phenolate represented by the formula (6) is heated, a phenoxyphospazene compound is produced by substitution of chlorine atoms with phenoxy groups. On the other hand, when a mixture of a dichlorophosphazene compound and alkali metal diphenolate represented by the formula (7) or (8) is heated, substitution reaction hardly proceeds.

Therefore, when a phenoxyphosphazene compound is prepared according to the method described in Japanese Unexamined Patent Publication No. 47,042/1976, which comprises reacting a dichlorophospazene compound with alkali metal phenolate and reacting the resulting compound with alkali metal diphenolate, it is highly difficult to completely substitute the chlorine atoms remaining after reaction, with alkali metal diphenolate. Even when one of the OM groups in the alkali metal diphenolate reacts with a chlorine atom in the dichlorophosphazene compound, the remaining OM group at the other end hardly reacts with a chlorine atom. When the OM group is converted to OH group, a hydroxyl-containing phosphazene compound results.

By contract, when a phenoxyphosphazene compound is prepared according to the method of the invention which comprises the steps of reacting a dichlorophosphazene compound with a mixture of alkali metal phenolate and alkali metal diphenolate and reacting the resulting compound with alkali metal phenolate, free hydroxyl groups do not remain in the molecule. M of both OM groups is eliminated from the alkali metal diphenolate so that the two oxygen atoms combine with phosphorus atoms in the dichlorophosphazene compound, thus giving a crosslinked phenoxyphosphazene compound (with an increased molecular weight).

The dichlorophosphazene compounds of the formula (4) and (5) for use as starting materials in the production process of the invention can be produced by known methods as described in Japanese Unexamined Patent Publication No. 87,427/1982, Japanese Examined Patent Publications Nos. 19,604/1983, 1363/1986 and 20,124/1987, etc. An exemplary method comprises reacting ammonium chloride and phosphorus pentachloride (or ammonium chloride, phosphorus trichloride and chlorine) at about 120 to 130° C. using chlorobenzene as a solvent, followed by removal of hydrogen chloride. According to this method, dichlorophosphazene compounds of the formula (4) and (5) can be obtained as a mixture.

According to the present invention, this mixture can be used per se as a starting compound, or can be separated into a cyclic dichlorophosphazene compound of the formula (4) and a straight- or branched-chain dichlorophosphazene compound of the formula (5) and either of them can be used singly.

Of dichlorophosphazene compounds represented by the formula (5), those wherein n is an integer of 3 to 1000 are preferred.

Examples of alkali metal phenolates represented by the formula (6) include a wide range of those known, and are sodium phenolate, potassium phenolate, lithium phenolate and so on. These alkali metal phenolates can be used either alone or in combination.

There is no limitation on the positions of two —OM groups (wherein M is as defined above) in alkali metal diphenolate of the formula (7). Any of ortho, metha and para will do. Examples of alkali metal diphenolates include alkali metal salts of resorcinol, hydroquinone, catechol and the like, of which sodium salts and lithium salts are preferred. These alkali metal diphenolates can be used either alone or in combination.

Examples of alkali metal diphenolates represented by the formula (8) include alkali metal salts of 4,4'-isopropylidenediphenol (bisphenol-A), 4,4'-sulfonyldiphenol (bisphenol-S), 4,4'-thiodiphenol, 4,4'-oxydiphenol, 4,4'-diphenol or the like, of which sodium salts and lithium salts are preferred. Alkali metal diphenolates are used either alone or in combination.

According to the present invention, alkali metal diphenolate of the formula (7) and alkali metal diphenolate of the formula (8) can be used either alone or in combination.

In the first step according to the production process of the invention, it is desirable to use alkali metal phenolate and alkali metal diphenolate in such amounts that not all chlorine atoms in the dichlorophosphazene compound are consumed by the reaction with alkali metal phenolate and alkali metal diphenolate, namely, some chlorine atoms in the dichlorophosphazene compound remain as they are after the reaction with alkali metal phenolate and alkali metal diphenolate. Consequently, —OM groups (wherein M is as defined above) at both sides in alkali metal diphenolate combine with phosphorus atoms of the dichlorophosphazene compound. In the first step, the alkali metal phenolate and the alkali metal diphenolate are used usually in such amounts that the combined amount of both phenolates, relative to the chlorine content of the dichlorophosphazene compound, is about 0.05 to 0.9 equivalents, preferably about 0.1 to 0.8 equivalents.

In the second step according to the production process of the invention, it is desirable to use alkali metal phenolate in an amount such that chlorine atoms and free hydroxyl groups in the compound obtained by the first step can be all consumed by the reaction with alkali metal phenolate. According to the present invention, the alkali metal phenolate is used usually in an amount of about 1 to 1.5 equivalents, preferably about 1 to 1.2 equivalents, relative to the chlorine content of the dichlorophosphazene compound.

According to the present invention, the ratio of the alkali metal phenolate (the total amount thereof used in the first and second steps) and alkali metal diphenolate (alkali metal diphenolate/alkali metal phenolate, molar ratio) is usually about 1/2000 to 1/4, preferably 1/20 to 1/6.

The reactions in the first step and the second step are carried out in an organic solvent, usually at a temperature between room temperature and about 150° C., preferably about 80 to 140° C. Examples of useful organic solvents are aromatic hydrocarbons such as benzene, toluene and xylene; and halogenated aromatic hydrocarbons such as monochlorobenzene and dichlorobenzene. The reactions are completed usually in about 1 to 12 hours, preferably about 3 to 7 hours.

The crosslinked phenoxyphosphazene compound of the invention obtained by the above reactions can be easily isolated and purified from the reaction mixture by a conventional isolation method such as washing, filtration, drying or the like.

The decomposition temperature of the crosslinked phenoxyphosphazene compound of the invention is usually in the range of 250 to 350° C.

The proportion of the phenyl groups in the crosslinked phenoxyphosphazene compound of the invention is 50 to 99.9%, preferably 70 to 90%, based on the total amount of the phenyl groups in the cyclic phenoxyphosphazene of the formula (1) and/or straight- or branched-chain phenoxyphosphazene of the formula (2).

The terminal groups $X^1$ and $Y^1$ in the formula (2) may vary in accordance with the reaction conditions and other factors. If the reaction is carried out under ordinary conditions, e.g., under mild conditions in a non-aqueous system, the resulting product will have a structure wherein $X^1$ is —N=P(OPh)$_3$ and $Y^1$ is —P(OPh)$_4$. If the reaction is carried out under such conditions that moisture or an alkali metal hydroxide is present in the reaction system, or under so severe conditions that a rearrangement reaction occurs, the resulting product will have a structure wherein $X^1$ is —N=P(OPh)$_3$ and $Y^1$ is —P(OPh)$_4$ and additionally a structure wherein $X^1$ is —N=P(O)OPh and $Y^1$ is —P(O)(OPh)$_2$.

The crosslinked phenoxyphosphazene compound of the invention is useful as a flame retardant for synthetic resins.

Flame-retardant Resin Composition

The flame-retardant resin composition of the present invention comprises a thermoplastic resin or a thermosetting resin, and the above crosslinked phenoxyphosphazene compound.

(a) Thermoplastic Resin

A wide variety of resins known in the art may be used as thermoplastic resin for use in the present invention. Such resins are, for example, polyethylene, polypropylene, polyisoprene, polyesters (polyethylene terephthalate, polybutylene terephthalate, etc.), polybutadiene, styrene resin, impact-resistant polystyrene, acrylonitrile-styrene resin (AS resin), acrylonitrile-butadiene-styrene resin (ABS resin), methyl methacrylate-butadiene-styrene resin (MBS resin), methyl methacrylate-acrylonitrile-butadiene-styrene resin (MABS resin), acrylonitrile-acrylic rubber-styrene resin (AAS resin), polymethyl (meth)acrylate, polycarbonate, modified polyphenylene ether (PPE), polyamide, polyphenylene sulfide, polyimide, polyether ether ketone, polysulfone, polyarylate, polyether ketone, polyether nitrile, polythioether sulfone, polyether sulfone, polybenzimidazol, polycarbodiimide, polyamideimide, polyetherimide, liquid crystalline polymer, composite plastics and the like.

Among these thermoplastic resins, polyester, ABS resin, polycarbonate, modified polyphenylene ether, polyamide, etc., are preferably used.

In the present invention, the thermoplastic resins may be used singly or in combination.

(b) Thermosetting Resin

A wide variety of resins known in the art may be used as the thermosetting resin for use in the present invention. Such thermosetting resins include polyurethane, phenol resin, melamine resin, urea resin, unsaturated polyester resin, diallyl phthalate resin, silicon resin and epoxy resin.

Among these thermosetting resins, particularly preferable are polyurethane, phenolic resin, melamine resin, epoxy resin, etc.

The epoxy resins are not limited to any specific types and may be selected from a wide variety of epoxy resins known in the art. Examples of such epoxy resins include bisphenol-A type epoxy resin, bisphenol-F type epoxy resin, bisphenol-AD type epoxy resin, phenol novolac type epoxy resin, cresol novolac type epoxy resin, cycloaliphatic epoxy resin, glycidyl ester-based resin, glycidyl amine-based epoxy resin, heterocyclic epoxy resin, urethane modified epoxy resin and brominated bisphenol-A type epoxy resin.

In the present invention, the thermosetting resins may be used singly or in combination.

The amount of the flame retardant (crosslinked phenoxy-phosphazene compound of the invention) relative to the thermoplastic resin or thermosetting resin is not particularly limited, but is 0.1–100 wt. parts, preferably 1–50 wt. parts, more preferably 5–30 wt. parts, based on 100 wt. parts of the thermoplastic resin or thermosetting resin.

(c) Inorganic Filler

The flame-retardant resin composition of the present invention may contain inorganic fillers to further enhance dripping preventing effect.

Conventionally, these inorganic fillers have been used mainly as reinforcements for improving the mechanical properties of resins. However, the inventors of the present invention have found that said flame retardants and inorganic fillers, when both are present in a resin, act synergistically and therefore are effective for improving the flame-retardant effects of the flame retardant, especially dripping preventive effect, as well as the mechanical properties of the resin.

When said flame retardant and the inorganic filler are both present in a resin, the surface layer of the resin becomes dense and reinforced. This prevents the diffusion of gases formed during combustion, and induces the formation of a char layer from the flame retardant, resulting in high flame-retardancy.

The inorganic fillers may be known fillers for resins. Examples of such fillers include mica, kaolin, talc, silica, clay, barium sulfate, barium carbonate, calcium carbonate, calcium sulfate, calcium silicate, titanium oxide, glass beads, glass balloons, glass flakes, glass fibers, fibrous alkali metal titanates (potassium titanate fibers, etc.), fibrous transition metal borates (aluminum borate fibers, etc.), fibrous alkaline earth metal borates (magnesium borate fibers, etc.), zinc oxide whisker, titanium oxide whisker, magnesium oxide whisker, gypsum whisker, aluminum silicate (mineralogical name: mullite) whisker, calcium silicate (mineralogical name: wollastonite) whisker, silicon carbide whisker, titanium carbide whisker, silicon nitride whisker, titanium nitride whisker, carbon fibers, alumina fibers, alumina-silica fibers, zirconia fibers, quartz fibers and the like.

Among these inorganic fillers, it is preferred to use fillers having shape anisotropy such as fibrous fillers, e.g., fibrous alkali metal titanates, fibrous transition metal borates, fibrous alkaline earth metal borates, zinc oxide whisker, titanium oxide whisker, magnesium oxide whisker, aluminum silicate whisker, calcium silicate whisker, silicon carbide whisker, titanium carbide whisker, silicon nitride whisker, titanium nitride whisker, and mica. More preferable are fibrous alkali metal titanates, fibrous transition metal borates, fibrous alkaline earth metal borates, titanium oxide whisker, calcium silicate whisker and the like.

These inorganic fillers may be used singly or in combination.

Among these inorganic fillers, those having shape anisotropy such as whiskers and mica are preferably used.

Examples of the potassium titanate fibers among inorganic fillers include potassium hexatitanate fibers having an average fiber diameter of about 0.05–2 μm and an average fiber length of about 1–500 μm, and preferably having an aspect ratio (fiber length/fiber diameter) of 10 or greater. Among them, potassium hexatitanate fibers having a pH ranging from 6 to 8.5 are more preferable. A pH of potassium titanate fibers mentioned herein refers to a pH, as determined at 20° C., of 1.0 wt. % of an aqueous suspension of potassium titanate fibers (in deionized water) which was stirred for 10 minutes. If the pH of the potassium titanate fibers is much higher than 8.5, physical properties of the resin and resistance to discoloration with heat may be disadvantageously decreased. On the other hand, when the pH is far below 6, the strength of the resulting resin composition is not effectively increased, and the residual acid may corrode processing machines and metallic molds. Hence it is not favorable.

The amount of the inorganic filler relative to the thermoplastic resin or thermosetting resin is not particularly limited. In view of a balance of improvements in mechanical properties and flame retardancy, however, the amount is 0.01–50 wt. parts, preferably 1–20 wt. parts, based on 100 wt. parts of the thermoplastic resin or thermosetting resin.

(d) Organic Phosphorus Compound Free of Halogen

The flame-retardant resin composition of the present invention may contain an organic phosphorus compound free of halogen (hereinafter referred to as "halogen-free organic phosphorus compounds") to further improve the flame retardancy thereof.

It is known that halogen-free organic phosphorus compounds are capable of improving the flame retardancy of the matrix such as resins. However, the inventors of the present invention found that when the specific phosphazene compounds for use in the present invention is used in combination with the halogen-free organic phosphorus compound, the flame-retardant effect is significantly increased due to synergism. The reason for this remarkable effect still remains to be elucidated. However, it is presumably because the conjoint use of these two compounds serves to form an expansion layer along with a char layer on the surface of the resin composition during combustion, and these layers suppress the diffusion of decomposition products and heat transfer.

A wide variety of halogen-free organic phosphorus compounds known in the art may be used in the present invention. For example, useful compounds include those disclosed in Japanese Examined Patent Publication No. 19003/1994, Japanese Unexamined Patent Publication No. 115262/1990, Japanese Unexamined Patent Publication No. 1079/1993, Japanese Unexamined Patent Publication No. 322277/1994, the specification of U.S. Pat. No. 5,122,556, etc.

Specific examples of the halogen-free phosphorus compound include trimethyl phosphate, triethyl phosphate, tributyl phosphate, trioctyl phosphate, triphenyl phosphate, tricresyl phosphate, trixylyl phosphate, cresyl diphenyl phosphate, xylyl diphenyl phosphate, tolyl dixylyl phosphate, tris(nonylphenyl) phosphate, (2-ethylhexyl) diphenyl phosphate and like phosphates; resorcinol diphenyl phosphate, hydroquinone diphenyl phosphate and like hydroxyl-containing phosphates; resorcinol bis(diphenyl phosphate), hydroquinone bis(diphenyl phosphate), bisphenol-A bis(diphenyl phosphate), bisphenol-S bis(diphenyl phosphate), resorcinol bis(dixylyl phosphate), hydroquinone bis(dixylyl phosphate), bisphenol-A bis(ditolyl phosphate), biphenol-A bis(dixylyl phosphate), bisphenol-S bis(dixylyl phosphate) and like condensed phosphate compounds; and trilauryl phosphine, triphenyl phosphine, tritolyl phosphine, triphenyl phosphine oxide, tritolyl phosphine oxide and like phosphine or phosphine oxide compounds.

Among these halogen-free organic phosphorus compounds, preferable are triphenyl phosphate, tricresyl phosphate, trixylyl phosphate, resorcinol bis(diphenyl phosphate), hydroquinone bis(diphenyl phosphate), bisphenol-A bis(diphenyl phosphate), resorcinol bis(dixylyl phosphate), hydroquinone bis(dixylyl phosphate), bisphenol-A bis(ditolyl phosphate) and like condensed phosphate compounds; and triphenyl phosphine oxide, tritolyl phosphine oxide and like phosphine oxide compounds. In particular, preferable are the compounds such as triphenyl phosphate, resorcinol bis(diphenyl phosphate), resorcinol bis(dixylyl phosphate), triphenyl phosphine oxide and the like.

These halogen-free organic phosphorus compounds may be used singly or in combination.

The amount of the halogen-free organic phosphorus compound relative to the thermoplastic resin or thermosetting resin is not particularly limited. In view of a balance of improvements in mechanical properties and flame retardancy, however, the amount of the halogen-free organic phosphorus compound is 0.1–50 wt. parts, preferably 1–30 wt. parts, based on 100 wt. parts of the thermoplastic resin or thermosetting resin. The amount of the flame retardant to be added thereto is 0.1–50 wt. parts, preferably 5–30 wt. parts, based on 100 wt. parts of the thermoplastic resin or thermosetting resin.

(e) Fluorine-containing Resin

Further, a fluorine-containing resin may be incorporated into the flame-retardant resin composition of the present invention containing a thermoplastic resin as a matrix within the range which does not adversely affect the object of the present invention. The amount of the fluorine-containing resin to be used is not particularly limited, but is 0.01–2.5 wt. parts, preferably 0.1–1.2 wt. parts, based on 100 wt. parts of the thermoplastic resins.

A wide variety of fluorine-containing resins known in the art may be used in the present invention. The examples include polytetrafluoroethylene resin (PTFE), tetrafluoroethylene-hexafluoropropylene copolymer resin (FEP), tetrafluoroethylene-perfluoroalkyl vinyl ether copolymer resin (PFA), tetrafluoroethylene-ethylene copolymer resin (ETFE), polychlorotrifluoroethylene resin (CTFE) and polyvinylidene fluoride (PVdF). Among these, PTFE is particularly preferable. By the addition of the fluorine-containing resins, the dripping preventing effect is produced in a more pronounced manner.

(f) Other Additives

The flame-retardant composition of the invention is a resin composition which does not contain a halogen (e.g., chlorine, bromine)-containing compound as a flame retardant component but can produce excellent flame retardant effects. One or more flame retardant additives conventionally used may be incorporated into the composition insofar as they do not adversely affect the excellent effects.

The flame retardant additive for use is not limited, and usually any additive that produces flame retardant effects can be used. Examples of useful flame retardant additives are metal oxides such as zinc oxide, tin oxide, iron oxide, molybdenum oxide, copper oxide and manganese dioxide; metal hydroxides such as aluminum hydroxide, magnesium hydroxide, zirconium hydroxide, oxalic acid-treated aluminum hydroxide and nickel compound-treated magnesium hydroxide; alkali metal salts or alkaline earth metal salts such as sodium carbonate, calcium carbonate, barium carbonate and sodium alkylsulfonate; organic chlorine compounds or organic bromine compounds such as chlorinated paraffin, perchlorocyclopentadecane, tetrabromobisphenol-A; epoxy resins, bis(tribromophenoxy)ethane and bis (tetrabromophthalimino)ethane; antimony compounds such as antimony trioxide, antimony tetraoxide, antimony pentaoxide and sodium antimonate; red phosphorus, halogen-containing phosphoric ester compounds, halogen-containing condensed phosphoric ester compounds or phosphonic acid ester compounds, nitrogen-containing compounds such as melamine, melamine cyanurate, melamine phosphate, melam, melem, mellon, succinoguanamine, guanidine sulfamate, ammoninum sulfate, ammonium phosphate, ammonium polyphosphate and alkylamine phosphate; boron compounds such as zinc borate, barium methaborate and ammonium borate; silicon compounds such as silicone polymers and silica; and thermally expansive graphite.

These flame retardant additives can be used singly or in combination.

Further, one or more conventional resin additives may be incorporated into the flame-retardant composition of the invention, insofar as they do not adversely affect the excellent properties. Examples of useful resin additives include flame retardants other than the aforementioned ones, dripping inhibitors (dropping inhibitors), UV absorbers, light stabilizers, antioxidants, light screens, metal deactivators, quenching agents, heat resistance stabilizers, lubricants, mold releasing agents, coloring agents, antistatic agents, antiaging agents, plasticizers, impact strength improving agents and compatibilizers.

The UV absorber is a component for absorbing light energy and releasing the absorbed light energy harmlessly in the form of heat energy by the transformation thereof into a keto form through intramolecular proton transfer (in the case of benzophenones and benzotriazoles) or by cis-trans isomerization (in the case of cyanoacrylates). Specific examples of UV absorbers include 2-hydroxybenzophenones such as 2,4-dihydroxybenzophenone, 2-hydroxy-4-methoxybenzophenone, 2-hydroxy-4-octoxybenzophenone and 5,5'-methylenebis(2-hydroxy-4-methoxybenzophenone); 2-(2'-hydroxyphenyl) benzotriazoles such as 2-(2'-hydroxy-5'-methylphenyl) benzotriazole, 2-(2'-hydroxy-5'-t-oetylphenyl)benzotriazole, 2-(2'-hydroxy-3',5'-di-t-butylphenyl)benzotriazole, 2-(2'-hydroxy-3',5'-di-t-butylphenyl)-5-chlorobenzotriazole, 2-(2'-hydroxy-3'-t-5'-methylphenyl)-5-chlorobenzotriazole, 2-(2'-hydroxy-3',5'-dicumylphenyl)benzotriazole and 2,2'-(methylenebis(4-t-octyl-6-benzotriazolyl)phenol; benzoates such as phenylsalicylate, resorcinol monobenzoate, 2,4-di-t-butylphenyl-3',5'-di-t-butyl-4'-hydroxybenzoate and hexadecyl-3,5-di-t-butyl-4-hydroxybenzoate; and substituted oxalic anilide such as 2-ethyl-2'-ethoxy oxalic anilide and 2-ethoxy-4'-dodecyl oxalic anilide; cyanoacrylates such as ethyl-α-cyano-β,β-diphenylacrylate and methyl-2-cyano-3-methyl-3-(p-methoxyphenyl)acrylate.

The light stabilizer is a component for decomposing hydroperoxides produced by light energy into stable N—O·radical, N—OR or N—OH, thereby providing light stability. For example, hindered amine light stabilizers can be used. Specific examples of light stabilizers include 2,2, 6,6-tetramethyl-4-piperidylstearate, 1,2,2,6,6-pentamethyl-4-piperidylstearate, 2,2,6,6-tetramethyl-4-piperidylbenzoate, bis(2,2,6,6-tetramethyl-4-piperidylsebacate, bis(1,2,2,6,6-pentamethyl-4-piperidyl) sebacate, tetrakis(2,2,6,6-tetramethyl-4-piperidyl)-1,2,3,4-butane tetracarboxylate, tetrakis(1,2,2,6,6-pentamethyl-4-piperidyl)-1,2,3,4-butanetetracarboxylate, bis(1,2,2,6,6- pentamethyl-4-piperidyl)-di(tridecyl)-1,2,3,4-butanetetracarboxylate, bis(1,2,2,6,6-pentamethyl-4-piperidyl)-2-butyl-2-(3',5'-di-t-butyl-4-hydroxybenzyl) malonate, 1-(2-hydroxyethyl)-2,2,6,6-tetramethyl-4-piperidinol/diethyl succinate polycondensate, 1,6-bis(2,2,6,6-tetramethyl-4-piperidylamino)hexane/dibromoethane polycondensate, 1,6-bis(2,2,6,6-tetramethyl-4-piperidylamino)hexane/2,4-dichloro-6-t-octylamino-s-triazine polycondensate, 1,6-bis(2,2,6,6-tetramethyl-4-piperidylamino)hexane/2,4-dichloro-6-morpholino-s-triazine polycondensate, and the like.

The antioxidant is a component for stabilizing peroxide radicals, such as hydroperoxy radicals, which are formed upon heat with molding or light exposure, or for decomposing generated peroxides, such as hydroperoxides. Examples of antioxidants include hindered phenol type antioxidants and peroxide decomposers. The hindered phenol type antioxidant acts as a radical chain-transfer inhibitor, and the peroxide decomposer decomposes peroxides generated in the reaction system into a stable alcohol, and prevents autoxidation.

Specific examples of hindered phenol type antioxidants include 2,6-di-t-butyl-4-methylphenol, styrenated phenol, n-octadecyl-3-(3,5-di-t-butyl-4-hydroxylphenyl)propionate, 2,2'-methylene bis(4-methyl-6-t-butylphenol), 2-t-butyl-6-(3-t-butyl-2-hydroxy-5-methylbenzyl)-4-methylphenylacrylate, 2-[1-(2-hydroxy-3,5-di-t-pentylphenyl)ethyl]-4,6-di-t-pentylphenylacrylate, 4,4'-butylidene bis(3-methyl-6-t-butylphenol), 4,41-thiobis(3-methyl-6-t-butylphenol), alkylated bisphenol, tetrakis[methylene-3-(3,5-di-t-butyl-4-hydroxyphenyl)proprionate] methane, 3,9-bis[2-{3-(3-t-butyl-4-hydroxy-5-methylphenyl)propionyloxy}-1,1-dimethylethyl]-2,4,8,10-tetraoxaspiro[5.5]undecane, and the like.

Examples of peroxide decomposers include organic phosphorus type peroxide decomposers such as tris(nonylphenyl) phosphite, triphenyl phosphate and tris(2,4-di-t-butylphenyl)phosphite; and organic thio type peroxide decomposers such as dilauryl-3,3'-thiodipropionate, dimyristyl-3,3'-thiodipropionate, distearyl-3,3'-thiodipropionate, pentaerythrityltetrakis(3-laurylthiopropionate), ditridecyl-3,3'-thiodipropionate and 2-mercaptobenzimidazole.

The light screen is a component for preventing light from penetrating into the bulk of a polymer. Specific examples of light screens include titanium oxide having a rutile structure ($TiO_2$), zinc oxide (ZnO), chromium oxide ($Cr_2O_3$) and cerium oxide ($CeO_2$).

The metal deactivator is a component for deactivating heavy metal ions in the resin by forming a chelate compound. Specific examples of metal deactivators include benzotriazoles and derivatives thereof (e.g. 1-hydroxybenzotriazole and the like).

The quenching agent is a component for deactivating photo-excited hydroperoxides and functional groups such as carbonyl groups in the polymer due to energy transfer. Useful quenching agents include organic nickel and the like.

In order to impart improved antifogging, antifungal, antimicrobial or like properties, other conventionally known additives may also be added.

Production of Flame-retardant Resin Compositions of the Invention

The flame-retardant resin composition of the invention can be produced by mixing a thermoplastic resin or a thermosetting resin and the aforementioned frame retardant, optionally together with an inorganic filler, a halogen-free organic phosphorus compound, a fluorine-containing resin, one or more flame retardant additives and other additives, in prescribed or proper amounts, followed by mixing and kneading the.mixture by a conventional method. For example, the mixture of components in the form of powder, beads, flakes or pellets is kneaded using an extruder, e.g., a uniaxial extruder or a biaxial extruder, or a kneader, e.g., Banbury mixer, a pressure kneader or a two-roll mill, giving a resin composition of the invention. When a liquid needs to be added, a conventional liquid injection device can be used and the mixture can be kneaded using the aforementioned extruder, kneader or the like.

Flame-retardant Resin Moldings of the Invention

The flame-retardant resin composition of the invention can be molded into flame-retardant resin moldings. For example, the resin composition can be molded into resin plates, sheets, films, special shapes or like extrusion moldings of various shapes using a conventional molding method such as press molding, injection molding or extrusion molding, or can be molded into a resin plate of two- or three-layered structure using a coextruder.

The thus-obtained flame-retardant resin composition and flame-retardant resin moldings of the invention can find wide application in various industrial fields, such as electrical, electronics or telecommunication industries, agriculture, forestry, fishery, mining, construction, foods, fibers, clothing, medical services, coal, petroleum, rubber, leather, automobiles, precision machinery, timber, furniture, printing, musical instruments, and the like.

Stated more specifically, the flame-retardant resin composition and flame-retardant resin moldings of the invention can be used for business or office automation equipment, such as printers, personal computers, word processors, keyboards, PDA (personal digital assistants), telephones, facsimile machines, copying machines, ECR (electronic cash registers), desk-top electronic calculators, electronic databooks, electronic dictionaries, cards, holders and stationery: electrical household appliances and electrical equipment such as washing machines, refrigerators, cleaners, microwave ovens, lighting equipment, game machines, irons and kotatsu (low, covered table with a heat source underneath); audio-visual equipment such as TV, VTR, video cameras, radio cassette recorders, tape recorders, mini discs, CD players, speakers and liquid crystal displays; and electric or electronic parts and telecommunication equipment, such as connectors, relays, condensers, switches, printed circuit boards, coil bobbins, semiconductor sealing materials, electric wires, cables, transformers, deflecting yokes, distribution boards, and clocks and watches.

Further, the flame-retardant resin composition and flame-retardant resin moldings of the invention can be widely used for the following applications: materials for automobiles, vehicles, ships, aircraft and constructions, such as seats (e.g., padding, outer materials), belts, ceiling covering, convertible tops, arm rests, door trims, rear package trays, carpets, mats, sun visors, wheel covers, mattress covers, air bags, insulation materials, hangers, hand straps, electric wire coating materials, electrical insulating materials, paints, coating materials, overlaying materials, floor materials, corner walls, deck panels, covers, plywood, ceiling boards, partition plates, side walls, carpets, wall papers, wall covering materials, exterior decorating materials, interior decorating materials, roofing materials, sound insulating panels, thermal insulation panels and window materials; and living necessities and sporting goods such as clothing, curtains, sheets, plywood, laminated fiber boards, carpets, entrance mats, seats, buckets, hoses, containers, glasses, bags, cases, goggles, skies, rackets, tents and musical instruments.

BEST MODE FOR CARRYING OUT THE INVENTION

The present invention will be specifically described below with reference to Synthesis Examples, Examples, Comparative Examples and Reference Examples, wherein parts and % mean weight parts and weight %, respectively. In addition, —Ph and —Ph— mean phenyl group and phenylene group, respectively. The evaluations in the Examples were carried out by the following methods.

1. Heat distortion temperature: Measured according to ASTM D-648 at a load of 18.6 kgf/cm$^2$, and used as an index of heat resistance.
2. Flame retardancy: Evaluated according to the test method of UL-94 (Test for Flammability of Plastic Materials for Parts in Devices and Appliances UL94, Fourth Edition), using test specimens each measuring 1/16 inch thick, 5 inches long and 0.5 inches wide.

Definitions in UL 94 are as follows.

| | |
|---|---|
| Afterflame | Persistence of flaming of a materials, after the ignition source has been removed. |
| Afteflame time | The length of time which a material continues to flame, under specified conditions, after the ignition source has been removed. |
| Afterglow | Persistence of glowing of a materials, after cessation of flaming or, if no flaming occurs, after removal of the ignition source. |
| Afterglow time | The length of time for which a material continues to glow under specified test conditions, after the ignition source has been removed and/or cessation of flaming. |
| $t_1$ | Afterflame time after first flame application. |
| $t_2$ | Afterflame time after second flame application. |
| $t_3$ | Afterglow time after second flame application. |

The material classification are specified as follows:

94V-0
  Afterflame time for each individual specimen $t_1$ or $t_2$: ≦10 sec.
  Total afterflame time for any condition set ($t_1$ plus $t_2$ for the 5 specimens): ≦50 sec.
  Afterflame plus afterglow time for each individual specimen after the second flame application ($t_2+t_3$): 30≦sec.
  Afterflame or afterglow of any specimen up to the holding clamp: No
  Cotton indicator ignited by flaming particles or drops: No 94V-1
  Afterflame time for each individual specimen $t_1$ or $t_2$: ≦30 sec.
  Total afterflame time for any condition set ($t_1$ plus $t_2$ for the 5 specimens): ≦250 sec.
  Afterflame plus afterglow time for each individual specimen after the second flame application ($t_2$ or $t_3$): ≦60 sec.
  Afterflame or afterglow of any specimen up to the holding clamp: No
  Cotton indicator ignited by flaming particles or drops: No 94V-2
  Afterflame time for each individual specimen $t_1$ or $t_2$: ≦30 sec.
  Total afterflame time for any condition set ($t_1$ plus $t_2$ for the 5 specimens): ≦250 sec.
  Afterflame plus afterglow time for each individual specimen after the second flame application ($t_2+t_3$): ≦60 sec.
  Afterflame or afterglow of any specimen up to the holding clamp: No
  Cotton indicator ignited by flaming particles or drops: Yes 3. Generation of volatile gas and discoloration at the time of molding: Inspected visually.

The thermoplastic resins, halogen-free organic phosphoric compounds and fluorine-containing resins used were as follows.

| | |
|---|---|
| PC | Aromatic polycarbonate resin (tradename: Iupilon S-2000N, a product of Mitsubishi Engineering Plastics Co., Ltd.) |
| ABS | ABS resin (tradename: Santac UT-61, a product of Mitsui Chemicals Inc.) |
| PBT | Polybutylene terephthalate resin (tradename: PBT-1200S, a product of Toray Industries, Inc.) |
| PPE/HIPS | Modified PPE (tradename: Xyron X-9108, a product of Asahi Chemical Co., Ltd.) |
| TPP | Triphenyl phosphate (a product of Wako Pure Chemical Industries, Ltd.) |
| TXP | Trixylyl phosphate (a product of Wako Pure Chemical Industries, Ltd.) |
| PTFE | Polytetrafluoroethylene (tradename: G-307, a product of Asahi Glass Co., Ltd.) |

SYNTHESIS EXAMPLE 1

Synthesis of Phenoxyphosphazene Compound Having p-Phenylene-crosslinked Structure A mixture of 103.5 g (1.1 moles) of phenol, 44.0 g (1.1 moles) of sodium hydroxide, 50 g of water and 500 ml of toluene was refluxed with heating, and water alone was removed from the system, giving a solution of sodium phenolate in toluene.

In parallel with the above reaction, 16.5 g (0.15 moles) of hydroquinone, 94.1 g (1.0 mole) of phenol, 31.1 g (1.3 moles) of lithium hydroxide, 52 g of water and 600 ml of toluene were placed in a 4-necked, 2-liter flask. The mixture was refluxed with heating, and water alone was removed from the system, giving a solution of lithium salts of hydroquinone and phenol in toluene. 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) was added dropwise to the toluene solution at 30° C. or lower with stirring, followed by reaction at 110° C. for 3 hours with stirring. To the reaction mixture was added the above prepared toluene solution of sodium phenolate with stirring, and the reaction was continued at 110° C. for 4 hours.

After the reaction was completed, the reaction mixture was washed three times with 1.0 liter of a 3% aqueous solution of sodium hydroxide and then three times with 1.0 liter of water, and the organic layer was concentrated under reduced pressure. The obtained concentrate was subjected to vacuum drying with heating at 80° C. at a pressure of 3 mmHg or less for 11 hours to give 211 g of crosslinked phenoxyphosphazene as a pale yellow powder.

The obtained crosslinked phoenoxyphosphazene had a hydrolyzable chlorine content of 0.04%, a weight average molecular weight (Mw) of 1100 (calculated as standard polystyrene, GPC analysis), and an approximate composition $$[N=P(-O\text{-p-}Ph-O-)_{0.15}(-O-Ph)_{1.7}]$$

which was found from the phosphorus content and CHN elemental analysis data.

The crosslinked phenoxyphosphazene obtained above did not show a definite melting point, and had a decomposition starting temperature of 306° C. and a 5% weight loss temperature of 311° C. as determined by the TG/DTA analysis (thermogravimetric analysis).

Further, the quantity of residual hydroxyl groups was determined by the acetylation method and found to be not larger than the detection limit ($1 \times 10^{-6}$ equivalents/g, as hydroxyl equivalent per 1 g of the sample). The detection limit is applied in the following Synthesis Examples.

SYNTHESIS EXAMPLE 2

Synthesis of Phenoxyphosphazene Compound Having 2,2-bis(p-Oxyphenyl)isopropyridene-crosslinked Structure 65.9 g (0.7 moles) of phenol and 500 ml of toluene were placed in a 4-necked, 1-liter flask, and while maintaining the internal temperature at 25° C., 14.9 g (0.65 gram atoms) of metallic sodium in the form of cut pieces was added thereto with stirring. After completion of the addition, stirring was continued for 8 hours at 77 to 113° C. until the metallic sodium was completely consumed, to thereby prepare a sodium phenolate solution.

In parallel with the above reaction, 57.1 g (0.25 moles) of bisphenol-A, 103.5 g (1.1 moles) of phenol and 800 ml of tetrahydrofuran (THF) were placed in a 4-necked, 3-liter flask, and while maintaining the internal temperature at 25° C. or lower, 11.1 g (1.6 gram atoms) of metallic lithium in the form of cut pieces was added thereto with stirring. After completion of the addition, stirring was continued for 8 hours at 61 to 68° C. until the metallic lithium was completely consumed. While maintaining the internal temperature at 20° C. or lower, 1.0 unit mole (115.9 g) of dichlorophosphazene oligomers (concentration 37%, monochlorobenzene solution 313 g, a mixture of 75% of trimer, 17% of tetramer, 6% of pentamer and hexamer, 1% of heptamer and 1% of octamer and higher oligomers) was added dropwise to the resulting slurry solution over 1 hour, followed by reaction at 80° C. for 2 hours. Subsequently, while maintaining the internal temperature at 20° C., the sodium phenolate solution separately prepared was added to the reaction mixture with stirring, followed by reaction at 80° C. for 5 hours.

After the reaction was completed, the reaction mixture was concentrated to remove THF, and 1 liter of toluene was added to the concentrate. The resulting toluene solution was washed three times with 1 liter of 2% NaOH aqueous solution and then three times with 1.0 liter of water, and the organic layer was concentrated under reduced pressure. The obtained concentrate was subjected to vacuum drying with heating at 80° C. at a pressure of 3 mmHg or less for 11 hours to give 229 g crosslinked phenoxyphosphazene as a white powder.

The obtained crosslinked phenoxyphosphazene had a hydrolyzable chlorine content of 0.07%, a weight average molecular weight (Mw) of 1130 (calculated as standard polystyrene, GPC analysis), and a composition $$[N=P(-O-Ph-C(CH_3)_2-Ph-O-)_{0.25}(-O-Ph)_{1.50}]$$

which was found from the phosphorus content and CHN elemental analysis data.

The obtained crosslinked phsnoxyphosphazene did not show a definite melting point, and had a decomposition starting temperature of 308° C. and a 5% weight loss temperature of 313° C. as determined by the TG/DTA analysis. The quantity of the residual hydroxyl groups was not larger than the detection limit (acetylation method).

SYNTHESIS EXAMPLE 3

Synthesis of Phenoxyphosphazene Compound Having m-Phenylene-crosslinked Structure The procedure of Synthesis Example 1 was followed using resorcinol in place of hydroquinone, to thereby obtain 209 g of crosslinked phoenoxyphosphazene as a white powder.

The obtained crosslinked phenoxyphosphazene had a hydrolyzable chlorine content of 0.08%, a weight average molecular weight (Mw) of 1080 (calculated as standard polystyrene, GPC analysis) and a composition $$[N=P(-O\text{-m-}Ph-O-)_{0.15}(-O-Ph)_{1.7}]$$

which was found from the phosphorus content and CHN elemental analysis data.

This crosslinked phenoxyphosphazene compound did not show a definite melting point, and had a decomposition starting temperature of 304° C., and a 5% weight loss temperature of 311° C. as determined by the TG/DTA analysis. The quantity of residual hydroxyl groups was not larger than the detection limit (acetylation method).

SYNTHESIS EXAMPLE 4

Synthesis of Phenoxyphosphazene Having 4,4'-Sulfonyldiphenylene(bisphenol-S Residue)-crosslinked Structure 103.5 g (1.1 moles) of phenol and 500 ml of THF were placed in a 4-necked, 1-liter flask, and while maintaining the internal temperature at 25° C., 25.3 g (1.1 gram atoms) of metallic sodium in the form of cut pieces was added thereto with stirring. After completion of the addition, stirring was continued for 5 hours at 65 to 72° C. until the metallic sodium was completely consumed.

In parallel with the above reaction, 94.1 g (1.0 mole) of phenol and 6.26 g (0.025 moles) of bisphenol-S were dissolved in 500 ml of THF in a 4-necked, 1-liter flask, and 24.1 g (1.05 gram atoms) of metallic sodium in the form of cut pieces was added thereto at 25° C. or lower with stirring. After completion of the addition, the temperature was elevated to 61° C. over 1 hour, and stirring was continued for 6 hours at 61 to 68° C., giving a mixed solution of sodium phenolate and disodium salt of bisphenol-S. The solution was added dropwise to 580 g of a 20% chlorobenzene solution containing 1.0 unit mole (115.9 g) of dichlorophosphazene oligomers (a mixture of 62% of trimer, 12% of tetramer. 11% of pentamer and hexamer, 3% of heptamer, 12% of octamer and higher oligomers) with cooling at 25° C. or lower and stirring, followed by reaction at 71 to 73° C. for 5 hours. Then, the sodium phenolate solution prepared above was added to the reaction mixture, and the reaction was continued at 71 to 73° C. for 3 hours.

After the reaction was completed, the reaction mixture was concentrated and dissolved again in 500 ml of chlorobenzene. The solution was washed three times with 5%

NaOH aqueous solution, once with 5% sulfuric acid, once with 5% aqueous sodium bicarbonate and three times with water. Then, the organic layer was concentrated and dried, giving 216 g of crosslinked phenoxyphosphazene as a pale yellow waxy product.

The obtained crosslinked phenoxyphosphazene had hydrolyzable chlorine content of 0.05%, a weight average molecular weight (Mw) of 1030 (calculated as standard polystyrene), and an approximate composition

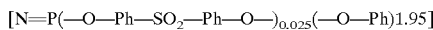
$$[N=P(-O-Ph-SO_2-Ph-O-)_{0.025}(-O-Ph)_{1.95}]$$

which was found from the phosphorus content and CHN elemental analysis data.

TG/DTA analysis; melting temperature Tm: 103° C., decomposition starting temperature: 321° C., 5% weight loss temperature: 332° C.

Quantity of residual hydroxyl groups: not larger than the detection limit (acetylation method).

SYNTHESIS EXAMPLE 5

Synthesis of Phenoxyphosphazene Having 4,4'-Sulfonyldiphenylene(bisphenol-S Residue)-crosslinked Structure Sodium phenolate was prepared following the procedure of Synthesis Example 4 and using 37.6 g (0.4 moles) of phenol and 9.2 g (0.4 gram atoms) of metallic sodium.

Further, a mixture of sodium phenolate and disodium salt of bisphenol-S was prepared following the procedure of Synthesis Example 4 and using 160.0 g (1.70 moles) of phenol, 12.5 g (0.05 moles) of bisphenol-S and 41.4 g (1.8 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) with cooling at 25° C. or lower and stirring. The subsequent procedure was carried out in the same manner as in Synthesis Example 4, giving 218 g of crosslinked phenoxyphosphazene as a pale yellow waxy product.

Analyses confirmed that the obtained crosslinked phenoxyphosphazene was the following compound.

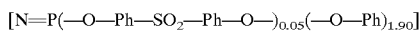
$$[N=P(-O-Ph-SO_2-Ph-O-)_{0.05}(-O-Ph)_{1.90}]$$

Residual chlorine: 0.01% or less

Weight average molecular weight Mw: 1080 (calculated as standard polystyrene)

TG/DTA analysis; melting temperature Tm: 103° C., decomposition starting temperature: 320° C., 5% weight loss temperature: 334° C.

Quantity of residual hydroxyl groups (acetylation method): not larger than the detection limit

SYNTHESIS EXAMPLE 6

Synthesis of Phenoxyphosphazene Having 4,4'-Sulfonyldiphenylene(bisphenol-S Residue)-crosslinked Structure Sodium phenolate was prepared following the procedure of Synthesis Example 4 and using 37.6 g (0.4 moles) of phenol and 9.2 g (0.4 gram atoms) of metallic sodium.

Further, a mixture of sodium phenolate and disodium salt of bisphenol-S was prepared following the procedure of Synthesis Example 4 and using 141.2 g (1.50 moles) of phenol, 37.5 g (0.15 moles) of bisphenol-S and 41.4 g (1.8 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer, 12% of octamer and higher oligomers) with cooling at 25° C. or lower and stirring. The subsequent procedure was carried out in the same manner as in Synthesis Example 4, giving 217 g of crosslinked phenoxyphosphazene as a pale yellow waxy product.

Analyses confirmed that the obtained crosslinked phenoxyphosphazene was the following compound.

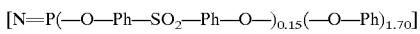
$$[N=P(-O-Ph-SO_2-Ph-O-)_{0.15}(-O-Ph)_{1.70}]$$

Residual chlorine: 0.03%

Weight average molecular weight Mw: 1150 (calculated as standard polystyrene)

TG/DTA analysis; melting temperature Tm: impossible to detect, decomposition starting temperature: 318° C., 5% weight loss temperature: 335° C.

Quantity of residual hydroxyl groups (acetylation method): not larger than the detection limit

SYNTHESIS EXAMPLE 7

Synthesis of Phenoxyphosphazene Having 4,4'-Oxydiphenylene-crosslinked Structure Sodium phenolate was prepared following the procedure of Synthesis Example 4 and using 94.1 g (1.0 mole) of phenol and 23.0 g (1.0 gram atoms) of metallic sodium.

Further, a mixture of sodium phenolate and disodium salt of bis(4-hydroxyphenyl)ether was prepared following the procedure of Synthesis Example 4 and using 94.1 g (1.0 mole) of phenol, 20.2 g (0.10 moles) of bis(4-hydroxyphenyl)ether and 27.6 g (1.2 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) with cooling at 25° C. or lower and stirring. The subsequent procedure was carried out in the same manner as in Synthesis Example 4, giving 211 g of crosslinked phenoxyphosphazene as a pale yellow waxy product.

Analyses confirmed that the obtained crosslinked phenoxyphosphazene was the following compound.

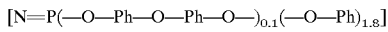
$$[N=P(-O-Ph-O-Ph-O-)_{0.1}(-O-Ph)_{1.8}]$$

Residual chlorine: 0.01% or less

Weight average molecular weight Mw: 1100 (calculated as standard polystyrene)

TG/DTA analysis; melting temperature Tm: impossible to detect, decomposition starting temperature: 321° C., 5% weight loss temperature: 328° C.

Quantity of residual hydroxyl groups (acetylation method): not larger than the detection limit

SYNTHESIS EXAMPLE 8

Synthesis of Phenoxyphosphazene Having 4,4'-Oxydiphenylene-crosslinked Structure Sodium phenolate was prepared following the procedure of Synthesis Example 4 and using 94.1 g (1.0 mole) of phenol and 27.6 g (1.2 gram atoms) of metallic sodium.

Further, a mixture of sodium phenolate and disodium salt of bis(4-hydroxyphenyl)ether was prepared following the procedure of Synthesis Example 4 and using 94.1 g (1.0 mole) of phenol and 40.4 g (0.20 moles) of bis(4-hydroxyphenyl)ether and 27.6 g (1.2 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) with cooling at 25° C. or lower and stirring. The subsequent procedure was carried out in the same manner as in Synthesis Example 4, giving 212 g of crosslinked phenoxyphosphazene as a pale yellow waxy product.

Analyses confirmed that the obtained crosslinked phenoxyphosphazene was the following compound.

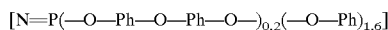

[N=P(—O—Ph—O—Ph—O—)$_{0.2}$(—O—Ph)$_{1.6}$]

Residual chlorine: 0.02%

Weight average molecular weight Mw: 1220 (calculated as standard polystyrene)

TG/DTA analysis; melting temperature Tm: impossible to detect, decomposition starting temperature: 306° C., 5% weight loss temperature: 321° C.

Quantity of residual hydroxyl groups (acetylation method): not larger than the detection limit

SYNTHESIS EXAMPLE 9

Synthesis of Phenoxyphosphazene Having 4,4'-Thiodiphenylene-crosslinked Structure Sodium phenolate was prepared following the procedure of Synthesis Example 4 and using 94.1 g (1.0 mole) of phenol and 23.0 g (1.0 gram atom) of metallic sodium.

Further, a mixture of sodium phenolate and disodium salt of 4,4'-thiophenol was prepared following the procedure of Synthesis Example 4 and using 94.1 g (1.0 mole) of phenol and 21.8 g (0.10 moles) of 4,4'-thiodiphenol and 27.6 g (1.2 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) with cooling at 25° C. or lower and stirring. The subsequent procedure was carried out in the same manner as in Synthesis Example 4, giving 215 g of crosslinked phenoxyphosphazene as a pale yellow highly viscous product.

Analyses confirmed that the obtained crosslinked phenoxyphosphazene was the following compound.

[N=P(—O—Ph—S—Ph—O—)$_{0.1}$(—O—Ph)$_{1.8}$]

Residual chlorine: 0.07%

Weight average molecular weight Mw: 1210 (calculated as standard polystyrene)

TG/DTA analysis; melting temperature Tm: impossible to detect, decomposition starting temperature: 337° C., 5% weight loss temperature: 342° C.

Quantity of residual hydroxyl groups (acetylation method): not larger than the detection limit

SYNTHESIS EXAMPLE 10

Synthesis of Phenoxyphosphazene Having 4,4'-Thiodiphenylene-crosslinked Structure

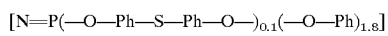

Sodium phenolate was prepared following the procedure of Synthesis Example 4 and using 94.1 g (1.0 mole) of phenol and 23.0 g (1.0 gram atom) of metallic sodium.

Further, a mixture of sodium phenolate and disodium salt of 4,4'-thiophenol was prepared following the procedure of Synthesis Example 4 and using 94.1 g (1.0 mole) of phenol, 43.7 g (0.20 g) of 4,4'-thiodiphenol and 27.6 g (1.2 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) with cooling at 25° C. or lower and stirring. The subsequent procedure was carried out in the same manner as in Synthesis Example 4, giving 217 g of crosslinked phenoxyphosphazene as a pale yellow highly viscous product.

Analyses confirmed that the obtained crosslinked phenoxyphosphazene was the following compound.

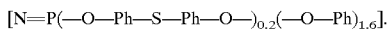

[N=P(—O—Ph—S—Ph—O—)$_{0.2}$(—O—Ph)$_{1.6}$].

Residual chlorine: 0.01%

Weight average molecular weight Mw: 1320 (calculated as standard polystyrene)

TG/DTA analysis; melting temperature Tm: impossible to detect, decomposition starting temperature: 341° C., 5% weight loss temperature: 347° C.

Quantity of residual hydroxyl groups (acetylation method): not larger than the detection limit

SYNTHESIS EXAMPLE 11

Synthesis of Phenoxyphosphazene Having 4,4'-Diphenylene-crosslinked Structure

Sodium phenolate was prepared following the procedure of Synthesis Example 4 and using 94.1 g (1.0 mole) of phenol and 23.0 g (1.0 gram atom) of metallic sodium.

Further, a mixture of sodium phenolate and disodium salt of 4,4'-diphenol was prepared following the procedure of Synthesis Example 4 and using 94.1 g (1.0 mole) of phenol, 18.6 g (0.10 moles) of 4,4'-diphenol and 27.6 g (1.2 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) with cooling at 25° C. or lower and stirring. The subsequent procedure was carried out in the same manner as in Synthesis Example 4, giving 208 g of crosslinked phenoxyphosphazene as a pale yellow highly viscous product.

Analyses confirmed that the obtained crosslinked phenoxyphosphazene was the following compound.

[N=P(—O—Ph—Ph—O—)$_{0.1}$(—O—Ph)$_{1.8}$]

Residual chlorine: 0.01%

Weight average molecular weight Mw: 1210 (calculated as standard polystyrene)

TG/DTA analysis; melting temperature Tm: impossible to detect, decomposition starting temperature: 338° C., 5% weight loss temperature: 349° C.

Quantity of residual hydroxyl groups (acetylation method): not larger than the detection limit

SYNTHESIS EXAMPLE 12

Synthesis of Phenoxyphosphazene Having 4,4'-Diphenylene-crosslinked Structure

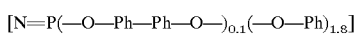

Sodium phenolate was prepared following the procedure of Synthesis Example 4 and using 94.1 g (1.0 mole) of phenol and 23.0 g (1.0 gram atom) of metallic sodium.

Further, a mixture of sodium phenolate and disodium salt of 4,4'-diphenol was prepared following the procedure of Synthesis Example 4 and using 94.1 g (1.0 mole) of phenol, 37.2 g (0.20 moles) of 4,4'-diphenol and 27.6 g (1.2 gram atoms) of metallic sodium. The mixture was added dropwise to 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) with cooling at 25° C. or lower and stirring. The subsequent procedure was carried out in the same manner as in Synthesis Example 4, giving 211 g of crosslinked phenoxyphosphazene as a pale yellow highly viscous product.

Analyses confirmed that the obtained crosslinked phenoxyphosphazene was the following compound.

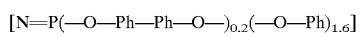

$[N=P(-O-Ph-Ph-O-)_{0.2}(-O-Ph)_{1.6}]$

Residual chlorine: 0.01%

Weight average molecular weight Mw: 1350 (calculated as standard polystyrene)

TG/DTA analysis; melting temperature Tm: impossible to detect, decomposition starting temperature: 336° C., 5% weight loss temperature: 347° C.

Quantity of residual hydroxyl groups (acetylation method): not larger than the detection limit

REFERENCE EXAMPLE 1

A mixture of 16.5 g (0.15 moles) of hydroquinone, 94.1 g (1.0 mole) of phenol, 31.1 g (1.3 moles) of lithium hydroxide, 52 g of water and 600 ml of toluene was placed in a 4-necked, 1-liter flask and refluxed with heating. Then, water alone was removed from the system, giving a solution of lithium salts and hydroquinone and phenol in toluene.

In parallel with the above reaction, a mixture of 103.5 g (1.1 moles) of phenol, 44.0 g (1.1 moles) of sodium hydroxide, 50 g of water and 500 ml of toluene was refluxed with heating, and water alone was removed from the system, giving a solution of sodium phenolate in toluene. 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) was added dropwise to the toluene solution at 30° C. or lower with stirring, followed by reaction at 110° C. for 3 hours with stirring. The above prepared toluene solution of sodium salts of hydroquinone and phenol was added to the reaction mixture with stirring, and the reaction was continued at 110° C. for 4 hours.

After the reaction was completed, the reaction mixture was washed three times with 1.0 liter of a 3% aqueous solution of sodium hydroxide, and then three times with 1.0 liter of water. Thereafter, the organic layer was concentrated under reduced pressure. The obtained concentrate was subjected to vacuum drying with heating at 80° C. at a pressure of 3 mmHg or less for 11 hours, giving 189 g of crosslinked phenoxyphosphazene as a pale yellow powder.

The obtained crosslinked phoenoxyphosphazene had a hydrolyzable chlorine content of 0.6%, and an approximate composition

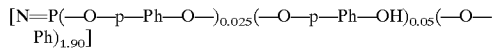

$[N=P(-O-p-Ph-O-)_{0.025}(-O-p-Ph-OH)_{0.05}(-O-Ph)_{1.90}]$ which was found from the phosphorus content and CHN elemental analysis data.

Weight average molecular weight Mw: 780 (calculated as standard polystyrene)

TG/DTA analysis; melting point: not definitely shown, decomposition starting temperature: 285° C.

Quantity of residual hydroxyl groups (acetylation method): 0.2 milliequivalents/g.

REFERENCE EXAMPLE 2

160.0 g (1.70 moles) of phenol, 12.5 g (0.05 moles) of bisphenol-S, 1.8 gram atoms of metallic sodium and 600 ml of toluene were placed in a 4-necked, 1-liter flask and refluxed with heating, giving a solution of sodium salts of bisphenol-S and phenol in toluene.

In parallel with the above reaction, a mixture of 37.6 g (0.4 moles) of phenol, 9.2 g (0.4 gram atoms) of metallic sodium and 500 ml of toluene was refluxed with heating, giving a solution of sodium phenolate in toluene. 580 g of a 20% chlorobenzene solution containing 1.0 unit mole (115.9 g) of dichlorophosphazene oligomers (a mixture of 62% of trimer, 12% of tetramer, 11% of pentamer and hexamer, 3% of heptamer and 12% of octamer and higher oligomers) was added dropwise to the toluene solution at 30° C. or lower with stirring. The subsequent procedure was carried out in the same manner as in Reference Example 1, giving 188 g of phenoxyphosphazene as a pale yellow waxy product.

The obtained phoenoxyphosphazene had a hydrolyzable chlorine content of 1.3%, and an approximate composition

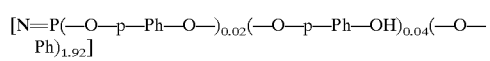

$[N=P(-O-p-Ph-O-)_{0.02}(-O-p-Ph-OH)_{0.04}(-O-Ph)_{1.92}]$ which was found from the phosphorus content and CHN elemental analysis data.

Weight average molecular weight Mw: 750 (calculated as standard polystyrene)

TG/DTA analysis; melting point: not definitely shown, decomposition starting temperature: 276° C.

Quantity of residual hydroxyl groups (acetylation method): 0.2 milliequivalents/g.

EXAMPLES 1 TO 13

Flame-retardant resin compositions according to the invention were prepared by adding each of the flame retardants (crosslinked phenoxyphosphazene compounds of the invention) shown in Table 1, optionally together with PTFE, to a resin comprising 75 parts of an aromatic polycarbonate resin and 25 parts of ABS resin, mixing the components in a mixer, and melting and kneading the mixture by means of a twin-screw kneader having a screw diameter of 25 mm.

COMPARATIVE EXAMPLE 1

A resin composition was prepared following the procedure of Example 1 and using trixylyl phosphate (TXP) in place of the crosslinked phenoxyphosphazene of Synthesis Example 1.

COMPARATIVE EXAMPLES 2 AND 3

Resin compositions were prepared following the procedure of Example 1 and using the phenoxyphosphazene obtained in Reference Example 1 or 2 in place of the crosslinked phenoxyphosphazene of Synthesis Example 1.

COMPARATIVE EXAMPLE 4

A resin composition was prepared following the procedure of Example 1 except that no flame retardant was added.

The resin compositions obtained in Examples 1 to 13 and Comparative Examples 1 to 4 were injection-molded to prepare test specimens having a thickness of 1/16 inch. Using the test specimens, the flame retardancy was evaluated according to the test method of UL-94, and the heat distortion temperature was measured according to ASTM D-648. The compositions were also checked for juicing during the molding process. The results are shown in Table 1.

TABLE 1

| | Flame retardant (part) | PTFE (part) | Flame retardancy UL-94 | Heat distortion temp. (° C.) | Juicing during molding |
|---|---|---|---|---|---|
| Example | | | | | |
| 1 | Syn.Ex.1 (12.5) | PTFE(0.2) | V-0 | 112 | No |
| 2 | Syn.Ex.2 (12.5) | PTFE(0.2) | V-0 | 115 | No |
| 3 | Syn.Ex.3 (12.5) | PTFE(0.2) | V-0 | 111 | No |
| 4 | Syn.Ex.1 (12.5) | — | V-0 | 110 | No |
| 5 | Syn.Ex.4 (12.5) | PTFE(0.2) | V-0 | 113 | No |
| 6 | Syn.Ex.5 (15.0) | — | V-0 | 114 | No |
| 7 | Syn.Ex.6 (12.5) | PTFE(0.2) | V-0 | 117 | No |
| 8 | Syn.Ex.7 (12.5) | PTFE(0.2) | V-0 | 114 | No |
| 9 | Syn.Ex.8 (12.5) | PTFE(0.2) | V-0 | 114 | No |
| 10 | Syn.Ex.9 (12.5) | PTFE(0.2) | V-0 | 112 | No |
| 11 | Syn.Ex.10(12.5) | PTFE(0.2) | V-0 | 113 | No |
| 12 | Syn.Ex.11(12.5) | PTFE(0.2) | V-0 | 116 | No |
| 13 | Syn.Ex.12(12.5) | PTFE(0.2) | V-0 | 118 | No |
| Comp. Ex. | | | | | |
| 1 | TXP (12.5) | PTFE(0.2) | V-2 | 82 | Yes |
| 2 | Ref.Ex.1 (12.5) | PTFE(0.2) | V-1 | 108 | Yes |
| 3 | Ref.Ex.2 (12.5) | PTFE(0.2) | V-1 | 108 | Yes |
| 4 | — | PTFE(0.2) | burned | 111 | — |

The above results demonstrate that the compounds of the invention are capable of exhibiting the desired flame retardancy in the absence of PTFE and are true non-halogen-based flame retardancy-imparting agents.

EXAMPLE 14

A flame-retardant resin composition was prepared by adding 15 parts of the crosslinked phenoxyphosphazene of Synthesis Example 1 to a resin sing 70 parts of poly(2,6-dimethyl-1,4-phenylene)oxide and 30 parts of rubber-modified impact resistant polystyrene, mixing the components in a mixer, and melting and kneading the mixture by means of a twin-screw kneader having a screw diameter of 25 mm.

EXAMPLES 15 TO 19

Flame-retardant resin compositions were prepared following the procedure of Example 14 and using the crosslinked phenoxyphosphazene obtained in Synthesis Examples 2, 3, 5, 8 or 10 in place of the crosslinked phenoxyphosphazene of Synthesis Example 1.

COMPARATIVE EXAMPLE 5

A resin composition was prepared following the procedure of Example 14 and using a condensed phosphoric acid diphenyl ester crosslinked by resocinol (a compound similar to a commercial product CR-733S available from Dathachi Chemical Industry Co., Ltd.) in place of the crosslinked phenoxyphosphazene of Synthesis Example 1.

COMPARATIVE EXAMPLE 6

A resin composition was prepared following the procedure of Example 14 and using the phenoxyphosphazene of Reference Example 1 in place of the crosslinked phenoxyphosphazene of Synthesis Example 1.

COMPARATIVE EXAMPLE 7

A resin composition was prepared following the procedure of Example 14 and using the phenoxyphosphazene of Reference Example 2 in place of the crosslinked phenokyphosphazene of Synthesis Example 1.

COMPARATIVE EXAMPLE 8

A resin composition was prepared following the procedure of Example 14 except that no flame retardant was added.

The resin compositions obtained in Examples 14 to 19 and Comparative Examples 5 to 8 were injection-molded to prepare test specimens having a thickness of 1/16 inch, and subjected to the flame retardancy evaluation according to the test method of UL-94 and the heat distortion temperature measurement according to ASTM D-648. The compositions were also checked for juicing during the molding. The results are shown in Table 2.

TABLE 2

| | Flame retardancy UL-94 | Heat distortion temp. (° C.) | Juicing during molding |
|---|---|---|---|
| Example | | | |
| 14 | V-0 | 130 | No |
| 15 | V-0 | 131 | No |
| 16 | V-0 | 128 | No |
| 17 | V-0 | 131 | No |
| 18 | V-0 | 133 | No |
| 19 | V-0 | 130 | No |
| Comp. Ex. | | | |
| 5 | V-2 | 110 | Yes |
| 6 | V-2 | 115 | Yes |
| 7 | V-2 | 112 | Yes |
| 8 | burned | 133 | — |

EXAMPLE 20

A flame-retardant resin composition of the invention was prepared by adding 5 parts of the crosslinked phenoxyphosphazene of Synthesis Example 1 to 100 parts of an aromatic polycarbonate resin, mixing the components in a mixer, and melting and kneading the mixture by means of a twin-screw kneader having a screw diameter of 25 mm.

This resin composition was injection-molded to prepare test specimens having a thickness of 1/16 inch. Using the test specimens, the flame retardancy of the composition was evaluated according to the test method of UL-94, and the heat distortion temperature thereof was measured according to ASTM D-648. The flame retardancy and heat distortion temperature were V-0 and 130° C., respectively. No juicing was observed during molding.

EXAMPLE 21

Test specimens were prepared following the procedure of Example 20 and using the crosslinked phenoxyphosphazene of Synthesis Example 5 in place of the crosslinked phenoxyphosphazene of Synthesis Example 1. Using the test specimens, evaluation was carried out in the same manner as in Example 20. The flame retardancy and heat distortion temperature of the resin composition were V-0 and 132° C., respectively. No juicing was observed during molding.

COMPARATIVE EXAMPLE 9

Test specimens were prepared following the procedure of Example 20 and using the phenoxyphosphazene of Reference Example 1 in place of the crosslinked phenoxyphosphazene of Synthesis Example 1. Using the test specimens, evaluation was carried out in the same manner as in Example 20. The flame retardancy and heat distortion temperature of the resin composition were V-2 and 118° C., respectively. Juicing was observed during molding.

COMPARATIVE EXAMPLE 10

Test specimens were prepared following the procedure of Example 20 except that no flame retardant was added. Using the test specimens, evaluation was carried out in the same manner as in Example 20. The flame retardancy and heat distortion temperature of the resin composition were V-2 and 132° C., respectively.

EXAMPLE 22

A flame-retardant resin composition of the invention was prepared by adding 12.5 parts of the crosslinked phenoxyphosphazene of Synthesis Example 3 to a resin comprising 70 parts of an aromatic polyearbonate resin and 30 parts of polybutylene terephthalate resin, mixing the components in a mixer, and melting and kneading the mixture by means of a twin-screw kneader having a screw diameter of 25 mm. This composition was made into test specimens and evaluated in the same manner as in Example 20. The flame retardancy and heat distortion temperature were V-0 and 130° C., respectively. No juicing was observed during molding.

EXAMPLE 23

A flame-retardant resin composition of the invention was prepared following the procedure of Example 22 and using the crosslinked phenoxyphosphazene of Synthesis Example 5 in place of the crosslinked phenoxyphosphazene of Synthesis Example 3. This composition was made into test specimens and evaluated in the same manner as in Example 20. The flame retardancy and heat distortion temperature of the resin composition were V-0 and 133° C., respectively. No Juicing was observed during molding.

COMPARATIVE EXAMPLE 11

A resin composition was prepared following the procedure of Example 22 and using the phenoxyphosphazene of Reference Example 2 in place of the crosslinked phenoxyphosphazene of Synthesis Example 3. This composition was made into test specimens and evaluated in the same manner as in Example 20. The flame retardancy and heat distortion temperature of the resin composition were V-2 and 125° C., respectively. Juicing was observed during molding.

COMPARATIVE EXAMPLE 12

A resin composition was prepared following the procedure of Example 22 except that no flame retardant was used. This composition was made into test specimens and evaluated in the same manner as in Example 20. The flame retardancy and heat distortion temperature of the resin composition were V-2 and 132° C., respectively.

EXAMPLE 24

A varnish was prepared by adding 10 parts of the crosslinked phenoxyphosphazene of Synthesis Example 1 to 100 parts of bisphenol-A type epoxy resin. A glass cloth was impregnated with the varnish and the impregnated glass cloth was dried to prepare a prepreg. Subsequently, a prescribed number of the prepregs were laminated on one another and the laminate was subjected to hot press at 160° C. or above to give a glass epoxy board having a thickness of 1/16 inch, which was then cut in a predetermined size to obtain test specimens. Using the test specimens, the flame retardancy was evaluated according to the test method of UL-94, and found to be V-0. No juicing was observed during hot press.

EXAMPLES 25 TO 28

Test specimens were prepared following the procedure of Example 24 and using the crosslinked phenoxyphosphazene of Synthesis Example 3, 5, 8 or 10 in place of the crosslinked phenoxyphosphazene of Synthesis Example 1. The flame retardancy of each resin composition was evaluated in the same manner as in Example 24, and found to be V-0. No juicing was observed during hot press.

COMPARATIVE EXAMPLE 13

Test specimens were prepared following the procedure of Example 24 and using a condensed phosphoric acid diphenyl ester crosslinked by resocinol (a compound similar to a commercial product CR-733S available from Daihachi Chemical Industry Co., Ltd.) in place of the crosslinked phenoxyphosphazene of Synthesis Example 1. The flame retardancy was evaluated in the same manner as in Example 24 and found to be V-2. Juicing was observed during hot press.

COMPARATIVE EXAMPLE 14

Test specimens were prepared following the procedure of Example 24 and using the phenoxyphosphazene compound of Reference Example 2 in place of the crosslinked phenoxyphosphazene of Synthesis Example 1. The flame retardancy was evaluated in the same manner as in Example 24, and found to be V-2. Juicing was observed during hot press.

COMPARATIVE EXAMPLE 15

Test specimens were prepared following the procedure of Example 24 except that no flame retardant was added. The flame retardancy was evaluated in the same manner as in Example 24. The test specimens burned, exhibiting no flame retardancy at all.

EXAMPLE 29

A flame-retardant resin composition of the invention was prepared by adding 12.5 parts of the crosslinked phenoxyphosphazene of Synthesis Example 5 and 7.5 parts of potassium titanate fibers (a product of Otsuka Chemical Co., Ltd., trade name: TISMO N-102, the same applies hereinafter) to a resin comprising 75 parts of an aromatic polycarbonate resin and 25 parts of ABS resin, mixing the components in a mixer, and melting and kneading the mixture by means of a twin-screw kneader having a screw diameter of 25 mm.

This composition was injection-molded to obtain test specimens having a thickness of 1/16 inch. Using the test specimens, the flame retardancy of the resin composition was evaluated according to the test method of UL-94, and the heat distortion temperature thereof was measured according to ASTM D-648. The composition was also checked for juicing during molding, generation of volatile gas during molding and discoloration of the test specimens after molding. The results are shown in Table 3.

EXAMPLES 30 TO 31

Flame-retardant resin compositions were prepared following the procedure of Example 29 and using kaolin or mica in place of the potassium titanate fibers. In the same manner as in Example 29, the compositions were made into test specimens and subjected to the flame retardancy evaluation and heat distortion measurement. The compositions were also checked for juicing during molding, generation of volatile gas during molding and discoloration of the test specimens after molding. The results are shown in Table 3.

EXAMPLE 32

A flame-retardant resin composition was prepared following the procedure of Example 29 except that 0.5 parts of PTFE was further added. In the same manner as in Example 29, the resin composition was made into test specimens and subjected to the flame retardancy evaluation and heat distortion measurement. The composition was also checked for juicing during molding, generation of volatile gas during molding and discoloration of the test specimens after molding. The results are shown in Table 3.

EXAMPLE 33

A flame-retardant resin composition was prepared following the procedure of Example 29 and using the crosslinked phenoxyphosphazene of Synthesis Example 7 in place of the crosslinked phenoxyphosphazene of Synthesis Example 5. In the same manner as in Example 29, the composition was made into test specimens and subjected to the flame retardancy evaluation and heat distortion measurement. The composition was also checked for juicing during molding, generation of volatile gas during molding and discoloration of the test specimens after molding. The results are shown in Table 3.

EXAMPLE 34

A flame-retardant resin composition was prepared following the procedure of Example 29 and using a resin comprising 70 parts of poly(2,6-dimethyl-1,4-phenylene)oxide and 30 parts of rubber-modified impact resistant polystyrene in place of the resin comprising 75 parts of an aromatic polycarbonate resin and 25 parts of ABS resin. In the same manner as in Example 29, the composition was made into test specimens and subjected to the flame retardancy evaluation and heat distortion measurement. The composition was also checked for juicing during molding, generation of volatile gas during molding and discoloration of the test specimens after molding. The results are shown in Table 3.

EXAMPLE 35

A varnish was prepared by adding 15 parts of the crosslinked phenoxyphosphazene of Synthesis Example 5 and 7.5 parts of potassium titanate fibers to 100 parts of bisphenol-A type epoxy resin. A glass cloth was impregnated with the varnish and the impregnated glass cloth was dried to prepare a prepreg. Subsequently, a prescribed number of the prepregs were laminated on one another, and the laminate was subjected to hot press at 160° C. or above to give a glass epoxy board having a thickness of 1/16 inch, and the board was cut in a predetermined size to obtain test specimens. The flame retardancy was evaluated according to the test method of UL-94 and the heat distortion temperature was measured according to ASTM D-648. Also, juicing during molding, generation of volatile gas during molding, and discoloration of the test specimens after molding were checked for. The results are shown in Table 3.

COMPARATIVE EXAMPLES 16 TO 18

Test specimens were prepared following the Example 29, 34 or 35 and using the phenoxyphosphazene of Reference Example 1 in place of the crosslinked phenoxyphosphazene compound of Synthesis Example 5, and the flame retardancy evaluation and heat distortion temperature measurement were carried out. Also, Juicing during molding, generation of volatile gas during molding and discoloration of the test specimens after molding were checked for. The results are shown in Table 3.

TABLE 3

|  | Flame retardancy UL-94 | Heat distortion temp. (° C.) | Juicing during molding | Volatile gas during molding | Discoloration during molding |
| --- | --- | --- | --- | --- | --- |
| Example |  |  |  |  |  |
| 29 | V-0 | 122 | No | No | No |
| 30 | V-0 | 129 | No | No | No |
| 31 | V-0 | 124 | No | No | No |
| 32 | V-0 | 122 | No | No | No |
| 33 | V-0 | 120 | No | No | No |
| 34 | V-0 | 140 | No | No | No |
| 35 | V-0 | — | No | No | No |
| Comp. Ex. |  |  |  |  |  |
| 16 | V-2 | 115 | Yes | Yes | Yes |
| 17 | V-2 | 136 | Yes | Yes | Yes |
| 18 | V-2 | — | No | No | Yes |

A flame-retardant resin composition was prepared by mixing in a mixer 100 parts of a resin composition comprising 75 parts of an aromatic polycarbonate resin and 25 parts of ABS resin, 5.0 parts of triphenyl phosphate, 5.0 parts of the crosslinked phenoxyphosphazene of Synthesis Example 5 and 0.6 parts of polytetrafluoroethylene (Trade name: G-307, a product of Asahi Glass Co., Ltd.), and melting and kneading the mixture by means of a twin-screw kneader having a screw diameter of 25 mm. In the same manner as in Example 29, the resin composition was made into test specimens and subjected to the flame retardancy evaluation and heat distortion temperature measurement. The composition was also checked for juicing during molding. The flame retardancy and heat distortion temperature were V-0 and 96° C., respectively. No juicing was observed during molding.

EXAMPLE 37

A flame-retardant resin composition was prepared following the procedure of Example 36 and using resorcinol bis(2,6-dimethylphenyl phosphate) in place of triphenyl phosphate. In the same manner as in Example 29, the resin composition was made into test and subjected to the flame retardancy evaluation and heat distortion temperature measurement. The composition was also checked for juicing during molding. The flame retardancy and heat distortion temperature were V-0 and 102° C., respectively. No juicing was observed during molding.

EXAMPLE 38

A flame-retardant resin composition was prepared following the procedure of Example 36 and using the crosslinked phenoxyphosphazene of Synthesis Example 10 in place of the crosslinked phenoxyphosphazene of Synthesis Example 5. In the same manner as in Example 29, the resin composition was made into test specimens and subjected to the flame retardancy evaluation and heat distortion temperature measurement. The composition was also checked for juicing during molding. The flame retardancy and heat distortion temperature were V-0 and 113° C., respectively. No juicing was observed during molding.

COMPARATIVE EXAMPLE 19

A flame-retardant resin composition was prepared following the procedure of Example 36 and using the phenoxyphosphazene of Reference Example 2 in place of the crosslinked phenoxyphosphazene of Synthesis Example 5. In the same manner as in Example 29, the resin composition was made into test specimens and subjected to the flame retardancy evaluation and heat distortion temperature measurement. The composition was also checked for juicing during molding. The flame retardancy and heat distortion temperature were V-2 and 109° C., respectively. Juicing was observed during molding.

EXAMPLE 39

A flame-retardant resin composition was prepared following the procedure of Example 36 using a modified-PPE resin (Trade name: Xyron X9108, a product of Asahi Chemical Co., Ltd.) in place of the mixture of polycarbonate resin and ABS resin. In the same manner as in Example 29, the resin composition was made into test specimens and subjected to the flame retardancy evaluation and heat distortion temperature measurement. The composition was also checked for juicing during molding. The flame retardancy and heat distortion temperature were V-0 and 130° C., respectively. No juicing was observed during molding.

COMPARATIVE EXAMPLE 20

A flame-retardant resin composition was prepared following the procedure of Example 39 using the phenoxyphosphazene of Reference Example 2 in place of the crosslinked phenoxyphosphazene of Synthesis Example 5. In the same manner as in Example 29, the resin composition was made into test specimens and subjected to the flame retardancy evaluation and heat distortion temperature measurement. The composition was also checked for juicing during molding. The flame retardancy and heat distortion temperature were V-2 and 125° C., respectively. Juicing was observed during molding.

What is claimed is:

1. A crosslinked phenoxyphosphazene compound characterized in that:
   at least one phosphazene compound selected from the group consisting of a cyclic phosphazene compound represented by the formula (1)

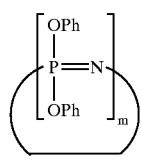

(1)

wherein m is an integer of 3 to 25 and Ph is phenyl group, and a straight- or branched-chain phosphazene compound represented by the formula (2)

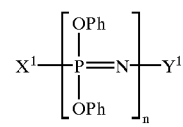

(2)

wherein $X^1$ represents a group —N=P(OPh)$_3$ or a group —N=P(O)OPh, $Y^1$ represents a group —P(OPh)$_4$ or a group —P(O)(OPh)$_2$, and n is an integer of 3 to 10000 and Ph is as defined above, is crosslinked with at least one crosslinking group selected from the group consisting of o-phenylene group, m-phenylene group, p-phenylene group and bisphenylene group represented by the formula (3)

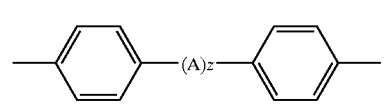

(3)

wherein A is —C(CH$_3$)$_2$—, —SO$_2$—, —S— or —O— and z is 0 or 1;
   (a) each of the crosslinking groups is interposed between the two oxygen atoms left after the elimination of phenyl groups from the phosphazene compound;
   (b) the amount of the phenyl groups in the crosslinked compound is 50 to 99.9% based on the total amount of the phenyl groups in said phosphazene compound represented by the formula (1) and/or said phosphazene compound represented by the formula (2); and
   (c) the crosslinked phenoxyphosphazene compound has no free hydroxyl groups in the molecule.

2. The crosslinked phenoxyphosphazene compound according to claim 1, prepared by the following steps:
   at least one dichlorophosphazene compound selected from the group consisting of a cyclic dichlorophosphazene compound represented by the formula (4)

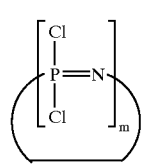

(4)

wherein m is as defined above, and a straight- or branched-chain dichlorophosphazene compound represented by the formula (5)

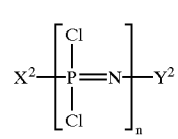

(5)

wherein $X^2$ represents a group —N=PCl$_3$ or a group —N=P(O)Cl, $Y^2$ represents a group —PCl$_4$ or a group —P(O)Cl$_2$, and n is as defined above, is reacted with a mixture of alkali metal phenolate represented by the formula (6)

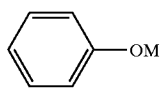 (6)

wherein M is an alkali metal, and at least one diphenolate selected from the group consisting of alkali metal diphenolate represented by the formula (7)

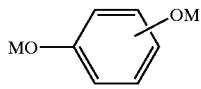 (7)

wherein M is as defined above and alkali metal diphenolate represented by the formula (8)

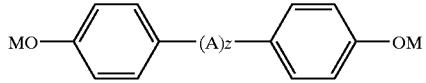 (8)

wherein A, z and M are as defined above; and the resulting compound is further reacted with the alkali metal phenolate represented by the formula (6).

3. A process for preparing the crosslinked phenoxyphosphazene compound defined in claim 1 which comprises the following steps:

at least one dichlorophosphazene compound selected from the group consisting of a cyclic dichlorophosphazene compound represented by the formula (4)

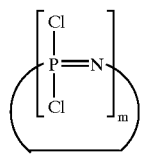 (4)

wherein m is an integer of 3 to 25, and a straight- or branched-chain dichlorophosphazene compound represented by the formula (5)

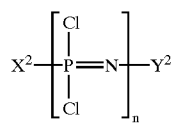 (5)

wherein $X^2$ represents a group —N=PCl$_3$ or a group —N=P(O)Cl, $Y^2$ represents a group —PCl$_4$ or a group —P(O)Cl$_2$, and n is an integer of 3 to 10000, is reacted with a mixture of alkali metal phenolate represented by the formula (6)

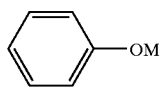 (6)

wherein M is an alkali metal and at least one diphenolate selected from the group consisting of alkali metal diphenolate represented by the formula (7)

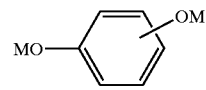 (7)

wherein M is as defined above and alkali metal diphenolate represented by the formula (8)

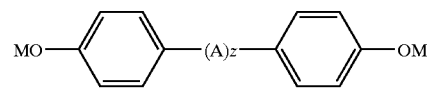 (8)

wherein M is as defined above, A is —C(CH$_3$)$_2$—, —SO$_2$—, —S— or —O— and z is 0 or 1; and the resulting compound is further reacted with the alkali metal phenolate represented by the formula (6).

4. A flame retardant comprising as an active ingredient the crosslinked phenoxyphosphazene compound defined in claim 1.

5. A flame-retardant resin composition comprising a thermoplastic resin or a thermosetting resin and the flame retardant defined in claim 4, the amount of the flame retardant being 0.1 to 100 wt. parts per 100 wt. parts of the resin.

6. A flame-retardant resin composition comprising a thermoplastic resin or a thermosetting resin, the flame retardant defined in claim 4 and an inorganic filler, the amount of the flame retardant being 0.1 to 100 wt. parts and the amount of the inorganic filler being 0.01 to 50 wt. parts, per 100 wt. parts of the resin.

7. A flame-retardant resin composition comprising a thermoplastic resin or a thermosetting resin, the flame retardant defined in claim 4 and a halogen-free organic phosphorus compound, the amount of the flame retardant being 0.1 to 50 wt. parts and the amount of the halogen-free organic phosphorus compound being 0.1 to 50 wt. parts, per 100 wt. parts of the resin.

8. A flame-retardant resin composition comprising a thermoplastic resin, the flame retardant defined in claim 4 and a fluorine-containing resin, the amount of the flame retardant being 0.1 to 100 wt. parts and the amount of the fluorine-containing resin being 0.01 to 2.5 wt. parts, per 100 wt. parts of the resin.

9. A flame-retardant resin molded article obtainable by molding the flame-retardant resin composition defined in claim 5, 6, 7 or 8.

10. A flame-retardant resin molded article comprising the crosslinked phenoxyphosphazene compound defined in claim 1 and a thermoplastic resin or a thermosetting resin.

11. A flame-retardant resin molded article comprising a thermoplastic resin or a thermosetting resin and the crosslinked phenoxyphosphazene compound defined in claim 1, the amount of the crosslinked phenoxyphosphazene compound being 0.1 to 100 wt. parts per 100 wt. parts of the resin.

12. A flame-retardant resin molded article comprising a thermoplastic resin or a thermosetting resin, the crosslinked phenoxyphosphazene compound defined in claim 1 and an inorganic filler, the amount of the crosslinked phenoxyphosphazene being 0.1 to 100 wt. parts and the amount of the inorganic filler being 0.01 to 50 wt. parts, per 100 wt. parts of the resin.

13. A flame-retardant resin molded article comprising a thermoplastic resin or a thermosetting resin, the crosslinked phenoxyphosphazene compound defined in claim 1 and a halogen-free organic phosphorus compound, the amount of the crosslinked phenoxyphosphazene compound being 0.1 to 50 wt. parts and the amount of the halogen-free organic phosphorus compound being 0.1 to 50 wt. parts, per 100 wt. parts of the resin.

14. A flame-retardant resin molded article comprising a thermoplastic resin, the crosslinked phenoxyphosphazene compound defined in claim 1 and a fluorine-containing resin, the amount of the crosslinked phenoxyphosphazene compound being 0.1 to 100 wt. parts and the amount of the fluorine-containing resin being 0.01 to 2.5 wt. parts, per 100 wt. parts of the thermoplastic resin.

\* \* \* \* \*